United States Patent [19]

Ennis, III

[11] Patent Number: 4,678,107

[45] Date of Patent: Jul. 7, 1987

[54] DRIPLESS DISPENSER FOR LIQUIDS AND VISCOUS FLUIDS

[75] Inventor: James F. Ennis, III, Preston, Conn.

[73] Assignee: Mark L. Anderson, Elmwood, Wis.

[21] Appl. No.: 762,305

[22] Filed: Aug. 2, 1985

[51] Int. Cl.⁴ .............................................. B67D 5/00
[52] U.S. Cl. ................... 222/386.5; 222/571; 604/228; 604/229
[58] Field of Search ............. 222/326, 327, 386, 386.5, 222/571; 604/228, 229, 900; 141/116, 117

[56] References Cited

U.S. PATENT DOCUMENTS

| | | | |
|---|---|---|---|
| 2,923,442 | 2/1960 | Maras | 222/327 |
| 2,955,728 | 10/1960 | Macklanburg | 222/386.5 |
| 3,029,985 | 4/1962 | Krueger et al. | 222/386.5 X |
| 3,174,655 | 3/1965 | Hurschman | 222/386.5 X |
| 3,250,443 | 5/1966 | Abbott | 222/386.5 X |
| 3,253,592 | 5/1966 | Von Pechmann | 222/386 X |
| 3,595,449 | 7/1971 | Stump et al. | 222/386 |
| 4,500,310 | 2/1985 | Christinger | 604/228 |

FOREIGN PATENT DOCUMENTS 537218 10/1955 Belgium ............................. 222/327

Primary Examiner—Joseph J. Rolla
Assistant Examiner—Frederick R. Handren
Attorney, Agent, or Firm—Edward H. Loveman

[57] ABSTRACT

A dispenser for liquids and viscous fluids has a syringe-like device with a barrel for containing fluid and a nozzle at one end. The plunger is movable axially in the barrel for discharging the fluid. At the inner end of the plunger is a flexible, elastic cap which has an end wall that is normally concave, but which is flattened out under pressure when the fluid is discharged. When pressure on the cap is removed, the cap reassumes its concave shape thereby creating a suction in the barrel which draws fluid back into the nozzle to prevent dripping.

7 Claims, 12 Drawing Figures

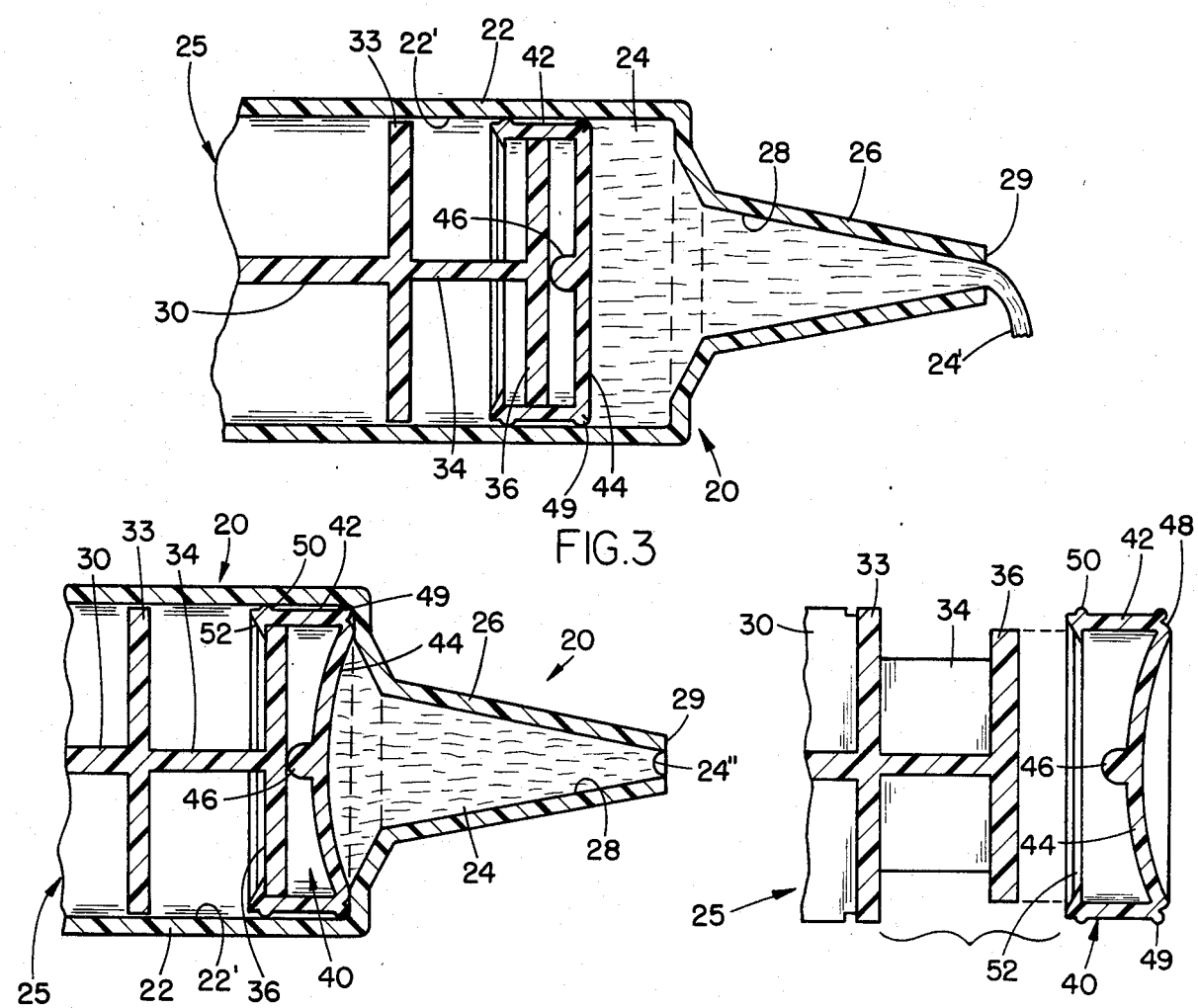
FIG.3
FIG.4
FIG.6
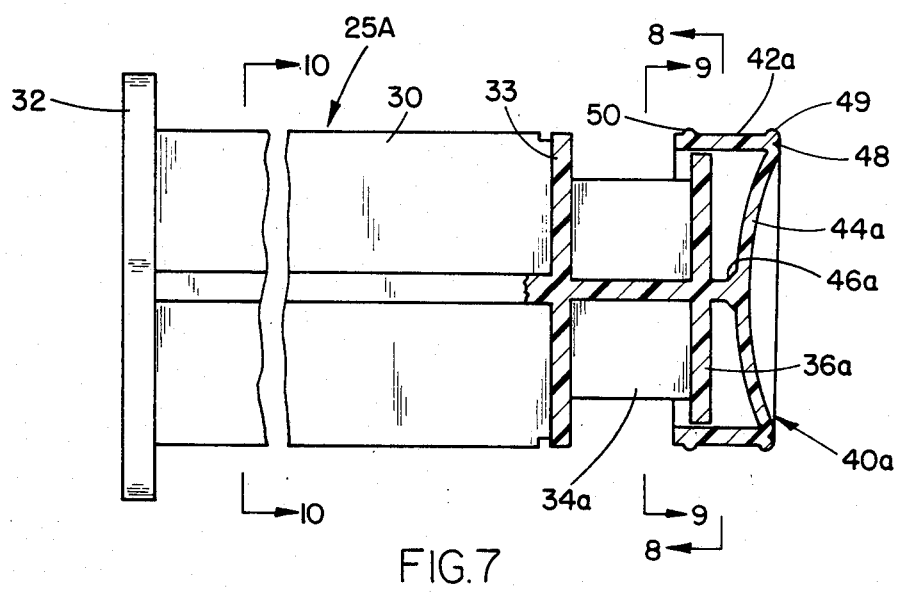
FIG.7

… … …

DRIPLESS DISPENSER FOR LIQUIDS AND VISCOUS FLUIDS

BACKGROUND OF THE INVENTION

1. Field of the Invention

This invention relates to the art of syringes and similar devices used for dispensing liquids and other fluids, and more particularly concerns a fluid dispensing device having a barrel for containing a fluid and a plunger provided with a concave elastic end for ejecting the fluid from the barrel.

2. Background of the Invention

Heretofore, syringes such as hypodermic syringes have been provided with plungers having rigid seals which eject liquid from the nozzle ends of the syringes. Such prior syringes all have the disadvantage that upon completion of ejection of a dose of liquid, one or more drops of liquid remaining in the nozzle drips out. This situation is objectionable, but no remedy for this problem has heretofore been proposed.

All prior syringes have had flat or curved seals which were made as rigid as possible to insure positive ejection of a required dose from the syringe. The same difficulty has been encountered with syringe-like devices used for dispensing caulking paste, grease, paint, putty, glue and other viscous fluids. After ejection of the fluids was completed, a stream or string of the viscous fluid trailed and dripped from the nozzle end of the dispensing device.

BRIEF DESCRIPTION OF THE INVENTION

The present invention is primarily directed at overcoming objectionable dripping of fluid from syringes, and syringe-like fluid dispensers from their nozzle openings. According to the invention, a rigid plunger is provided for ejecting fluid from the barrel of a syringe. Mounted on the inner end of the plunger is an elastic, concave seal which assumes a flat configuration when force is appled to the plunger or rod to eject fluid from the barrel of the syringe. When the plunger stops advancing in the barrel, the seal reassumes its normal concave configuration, which induces a negative pressure in the nozzle of the device. This negative pressure or suction results in withdrawal of the fluid into the nozzle from its free open end, so that dripping therefrom is effectively prevented. It desired, the concave elastic seal may be a separate member which is snapped or screwed on the inner end of the plunger of snapped into a barrel or may be made integral with the plunger. The invention is applicable to all types of syringes and syringe-like fluid dispensers having a barrel terminating in a nozzle or open end from which fluid or paste is dispensed, and a seal movable axially in the barrel to force the fluid out of the nozzle.

These and other objects and many of the attendant advantages of this invention will be readily appreciated as the same becomes better understood by reference to the following detailed description when considered in connection with the accompanying drawings in which:

BRIEF DESCRIPTION OF THE DRAWINGS

FIG. 3 is an enlarged fragmentary central sectional view taken along line 3—3 of FIG. 1;

FIG. 4 is a framentary sectional view similar to a portion of FIG. 3, showing the configuration of the elastic, concave plunger seal or end when ejection of fluid is complete;

FIG. 6 is an enlarged fragmentary axial sectional view taken along line 6—6 of FIG. 5;

FIG. 7 is a side elevational view partially in axial section of another plunger for a syringe-like fluid ejection device;

DESCRIPTION OF THE PREFERRED EMBODIMENT

Figure 1:
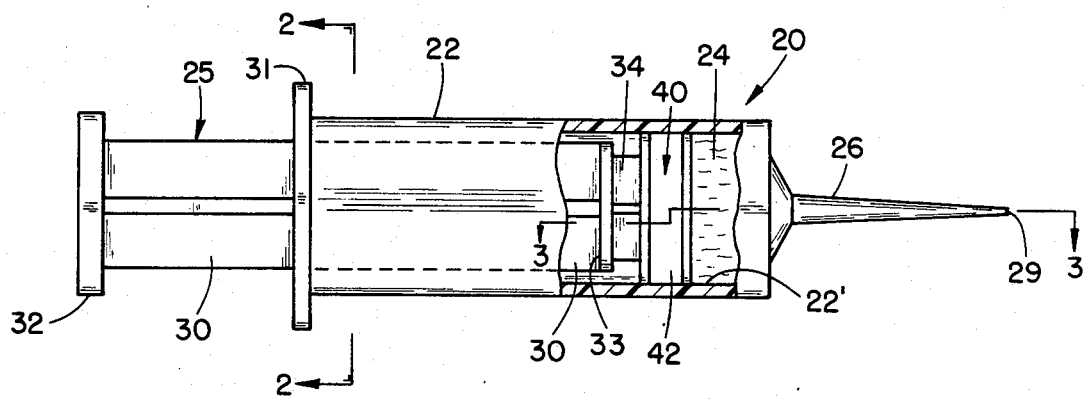
FIG. 1 is a side elevational view, with side wall partially broken away, showing a fluid dispenser or syringe embodying the invention.
Figure 2:
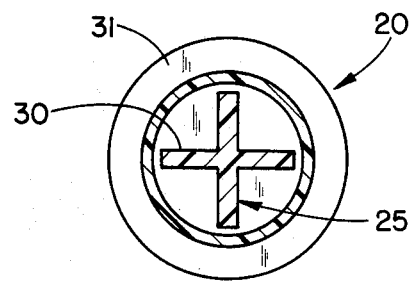
FIG. 2 is a cross sectional view taken along line 2—2 of FIG. 1.
Figure 5:
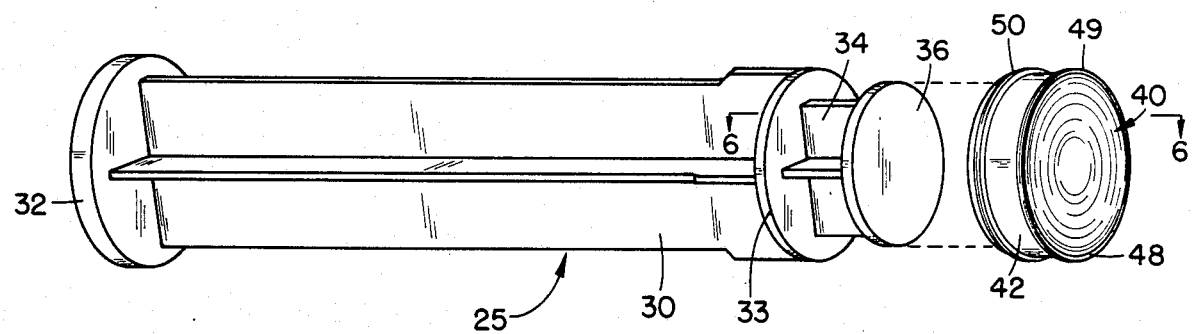
FIG. 5 is an exploded perspective view of parts of the plunger used in the fluid ejection device of FIGS. 1-4.
Figure 8:
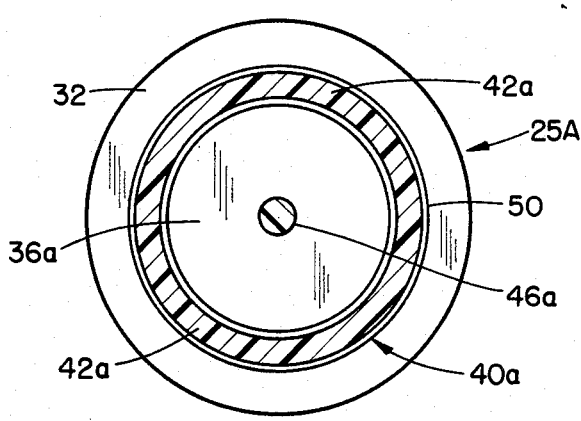
FIGS. 8, 9, and 10 are cross sectional views taken along line 8—8, 9—9, and 10—10 respectively of FIG. 7.
Figure 9:
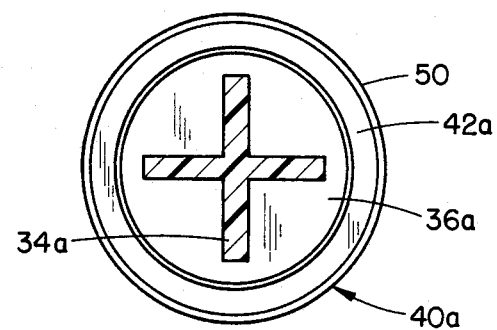
Figure 10:
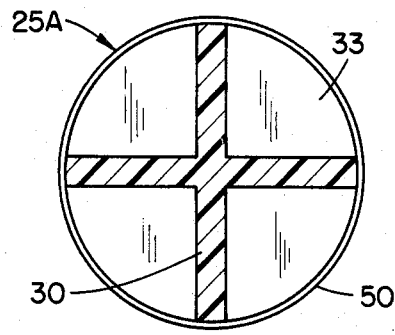
Figure 11:
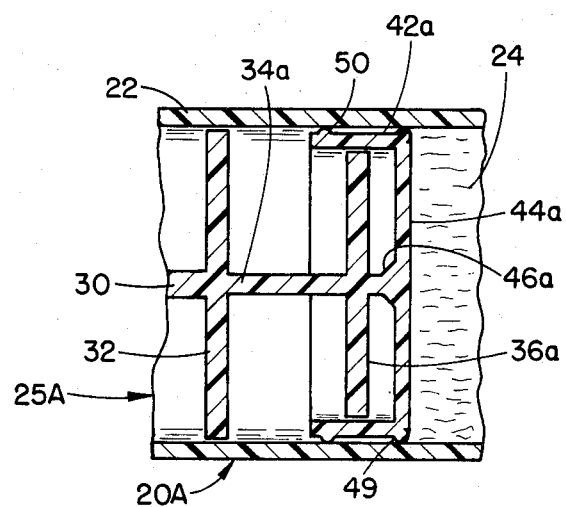
FIG. 11 is a fragmentary axial sectional view similar to a portion of FIG. 3, showing the plunger of FIGS. 7-10 in operation in a fluid dispenser.

Referring now to the drawings wherein like reference characters designate like or corresponding parts throughout, there is illustrated in FIGS. 1-4, a syringe or syringe-like device generally designated as reference numeral 20 having a cylindrical barrel 22 for containing a fluid 24 to be dispensed from a nozzle 26 at one end of the barrel. The nozzle 26 has a tapered passage 28 open at its free end 29 out of which the fluid 24 flows.

A plunger 25 is inserted in the distal open end of the barrel 22 which has an annular flange 31 thereat. The plunger 25 as best shown in FIGS. 2-6 to which reference is now made, is a rigid structure having mutually orthogonal ribs or splines 30. A knob is integral with the distal end of the ribs 30. At the other, inner end of the plunger 25 is a plate 33 disposed perpendicular to the axis of the plunger 25 and having a diameter smaller than the internal diameter of the barrel 22. Extending longitudinally from the plate 33 are further short ribs or splines 34 which terminate with a rigid round disk 36 disposed parallel to plate 32. A generally cylindrical cap or seal 40 engages on the disk 36.

The cap 40 has a cylindrical body 42 terminating at one end in an elastic circular wall 44 which is externally concave. The wall 44 can assume a flat configuration as best shown in FIG. 3. At the convex inner side of the wall 44 is a small centrally located knob or tit 46. The cylindrical body 42 is formed with a circular groove 48 at its front end which relieves the radial and circumferential stress of the elastic wall 44 when it is forced into a flat position. Normally, the wall 44 will revert to the externally concave configuration when axial pressure thereon is released. An annular bead 49 at the front end of the cap 40 extends radially of cylindrical body 42 and forms a circumferential seal with the inner wall 22' of the barrel 22. Another radially extending, circumferential annular bead 50 at the rear open end of the body 42 defines another circumferential seal with the inner wall 22' of the barrel 22. A further circumferential bead 52 is located at the inner side of the body 42 at its open rear end. The bead 52 engages the disk 36 and prevents the cap from separating therefrom. The disk 36 is somewhat movable, axially, inside the cap 40.

To use the device, the cap 40 is snapped on the disk 36 of the plunger 25. Then the syringe or fluid dispensing device 20 is filled with a required amount of fluid 24. Then the plunger 25 is inserted into the barrel 22. Alternatively, the plunger 25, may be inserted fully into the barrel 22, and fluid be drawn in by suction by axial outward movement of the plunger 25. Axial pressure, exerted inwardly upon the plunger 25 will force fluid 24 out of the nozzle 26 in a stream 24' as clearly shown in FIG. 3. When pressure is exerted on the plunger 25, the elastic wall 44 will assume a flat position. The knob 46 will be in contact with the disk 36 which moves slightly forward away from the bead 52. After the desired amount of fluid is dispensed, pressure on the plunger 25 will be released. This will permit the axially stressed wall 44 of the cap 40 to reassume its externally concave position, and at the same time, the fluid 24 in the nozzle 26 will be drawn toward the cap as shown best in FIG. 4. Due to capillarity the end surface 24" of the fluid nozzle 26 will assume a concave configuration, thus dripping of the fluid 24 from the nozzle 26 is prevented.

In FIGS. 7–11 there is shown another plunger 25A which may be used in a syringe or syringe-like device 20A in place of the plunger 25. Here an externally concave elastic end wall 44a of a cap 40a is integral with a cylindrical wall or body 42a at the front end of the plunger 25a. Mutually perpendicular rigid splines 34a are integral with a round disk 36a. The disk 36a is connected to an elastic wall 44a by an integral central stem 46a. The external axially spaced annular sealing beads 49, 50, are provided on the cylindrical wall 42a. The circular groove 48 at the front end of the cap 40a relieves pressure when the elastic end wall 44a is stressed to the flat configuration.

Figure 12:
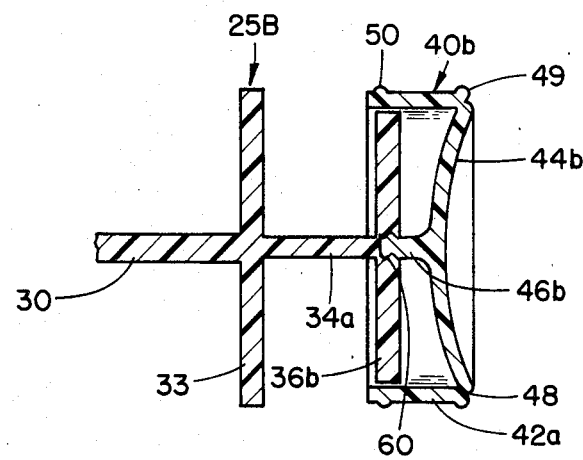
FIG. 12 is a side elevational view partially in section, similar to a portion of FIG. 3, showing a further plunger construction.

A plunger 25B shown in FIG. 12 has an end cap 40b similar to the cap 40a. Here, however, a central stem 46b is provided with a threaded rear end which screws into a threaded recess 60 at the center of the forward side of a disk 36b.

Both of the plungers 25A and 25B operate in the same manner. Upon application of manual pressure on the rigid plunger 25A or 25B, normally concave elastic wall 44a or 44b of the respective cap 40a, or 40b assume a flat configuration due to application of resisting pressure by the fluid 24 in the syringe barrel 22. The respective disk 36a, or 36b moves forward with respective stem 46a and 46b while the end wall 44a or 44b flattens out; see FIG. 11. Upon release of pressure, the stress in the elastic cup wall 44a, or 44b is relieved, and the end wall reassumes its normal externally concave configuration. At the same time, the wall creates a suction which draws the fluid 24 inwardly of the nozzle 29 as illustrated in FIG. 4. The plunger 25AA has the advantage that the cap and plunger body are fabricated in one piece. Since, the plunger body must be rigid while the cap is flexible and elastic, the constuction of FIG. 6 or FIG. 12 may be preferred, since the cap and plunger body may be manufactured separately and then the cap and plunger body may be easily attached to each other.

All of the plungers 25, 25A, and 25B may be used in a fluid dispensing syringe-like device for ejecting liquid or viscous fluid. Any liquid suitable for dispensing by syringe may be used. A viscous fluid may be by way of example a caulking compound, putty, paste, paint, glue, grease, etc . . . . In all embodiments of the invention, the construction of the dispensing device with its movable, elastic cap insures that no fluid drips from the nozzle of the device after manual pressure on the plunger handle 15 or rod is released.

It should be understood that the foregoing relates to only a limited number of preferred embodiments of the invention, which have been by way of example only, and that it is intended to cover all changes and modifications of the example of the invention herein chosen for the purpose of the disclosure, which do not constitute departures from the spirit and scope of the invention.

What is claimed is:

1. A fluid dispensing device, comprising:
   a cylindrical barrel for containing a fluid to be dispensed;
   a nozzle at a forward end of said barrel for discharging fluid from barrel, said barrel having an open rear end;
   an elongated plunger having one end insertable axially into said barrel through said open rear end thereof; and a cup-shaped cylindrical cap fitted to said one end of said plunger in said barrel, said cap having an axially extending sidewall with external circumferential beading providing fluid tight sealing between said cap and said barrel and having a flexible, elastic externally concave end wall for applying pressure to fluid in said barrel to force the same out of said nozzle when said plunger is axially advanced in said barrel, said one end of said plunger being disposed adjacent to and confronting an internal side of said end wall, the internal side of said end wall being formed convexly, said end wall of said cap being sufficiently flexible and elastic to assume an axially stressed, flattened out configuration when a forwardly directed force is applied to the internal side of said end wall by said one end of said plunger upon advancement of said plunger in said barrel, and to reassume said external concave configuration when said force and stress are released, thereby creating a suction in said barrel ahead of said end wall to draw back fluid in said nozzle and prevent dripping of fluid from said nozzle;
   said end wall of said cap having formed on the external surface thereof, where the end wall is joined to the sidewall, a circumferentially extending, peripheral groove providing a reduced thickness region to relieve radial and circumferential pressure on said end wall when said end wall is flattened out under axial stress; and
   a knob centrally located on said internal convex side of said end wall for contact by said one end of said plunger, such that said end wall will assume a flat position when a forwardly directed force is exerted thereon by said one end of said plunger.

2. A fluid dispensing device as defined in claim 1, wherein said plunger is a rigid member, and wherein said cap is axially slidable on said member.

3. A fluid dispensing device as defined in claim 2, wherein said one end of said plunger is a disk having a diameter smaller then that of said cylindrical cap so that said cap slides axially on said plunger when said end wall of said cap assumes both said flattened and concave configurations.

4. A fluid dispensing device as defined in claim 3, wherein said cap has internal beading to enable said cap to snap fit onto said disk.

5. A fluid dispensing device as defined in claim 1, wherein said one end of said plunger is centrally attached to said knob for applying pressure to said cap against said fluid in barrel to cause said end wall to assume said flattened out configuration while fluid is being discharged from said nozzle.

6. A fluid dispensing device as defined in claim 5, wherein said plunger is integrally formed with said knob.

7. A fluid dispensing device as defined in claim 5, wherein said knob is comprised of a threaded stem which mates with an internal thread in said one end of said plunger.

* * * * *